United States Patent [19]

Hwang

[11] Patent Number: 5,116,366
[45] Date of Patent: May 26, 1992

[54] PROSTHETIC HEART VALVE

[75] Inventor: Ned H. C. Hwang, Memphis, Tenn.

[73] Assignees: Ned H. S. Hwang, Memphis, Tenn.; Onx, Inc., Del.

[21] Appl. No.: 392,745

[22] Filed: Aug. 11, 1989

[51] Int. Cl.⁵ .............................................. A61F 2/24
[52] U.S. Cl. ..................................... 623/2; 137/512.1; 137/527.8
[58] Field of Search ................ 623/2; 137/512.1, 527.8

[56] References Cited

U.S. PATENT DOCUMENTS

| | | | |
|---|---|---|---|
| 4,011,601 | 3/1977 | Clune et al. | 3/1.5 |
| 4,078,268 | 3/1978 | Possis | 3/1.5 |
| 4,123,805 | 11/1978 | Kramer et al. | 3/1.5 |
| 4,159,543 | 7/1979 | Carpentier | 3/1.5 |
| 4,373,216 | 2/1983 | Klawitter | 3/1.5 |
| 4,425,670 | 1/1984 | Figuera | 3/1.5 |
| 4,484,365 | 11/1984 | Murguet et al. | 3/1.5 |
| 4,535,484 | 8/1985 | Marconi | 3/1.5 |
| 4,692,165 | 9/1987 | Bokros | 623/2 |
| 4,872,875 | 10/1989 | Hwang | 3/2 |
| 4,892,540 | 1/1990 | Vallana | 623/2 |

Primary Examiner—David J. Isabella
Assistant Examiner—Stephanie L. Iantorno
Attorney, Agent, or Firm—Fitch, Even, Tabin & Flannery

[57] ABSTRACT

Disclosed is a heart valve of the bi-leaflet type having an improved hinge arrangement that allows the valve to respond more quickly to flow reversal and minimizes fluttering of the leaflets in the open position. The leaflets are slidably and pivotally mounted in a heart valve body for movement between closed and open positions. The leaflets have notches which matingly engage complementary surfaces on pivot projections extending inward from the valve body sidewall. The shape and relationship of these complementary surfaces provides for improved operating characteristics.

20 Claims, 3 Drawing Sheets

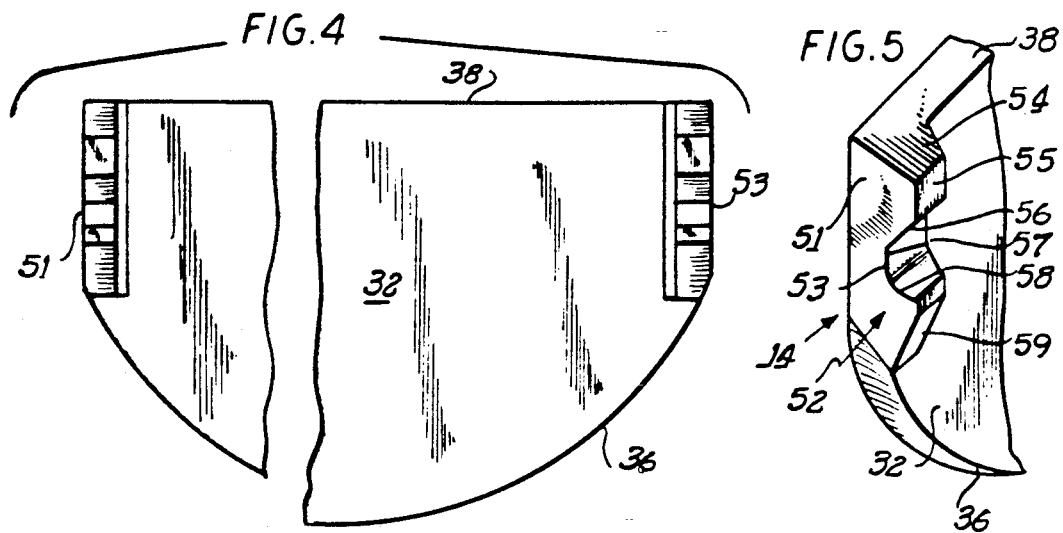
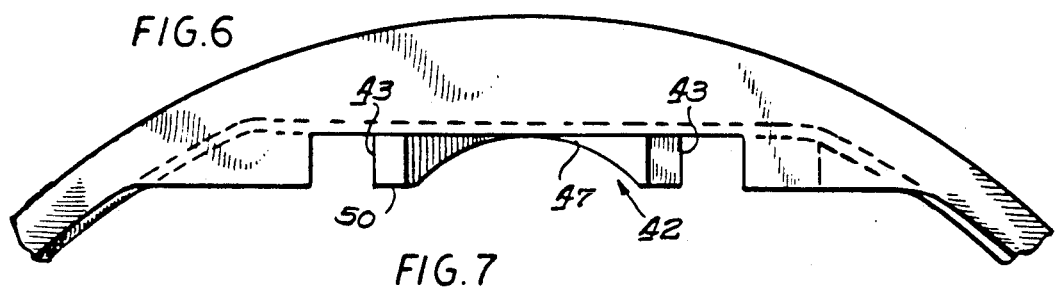
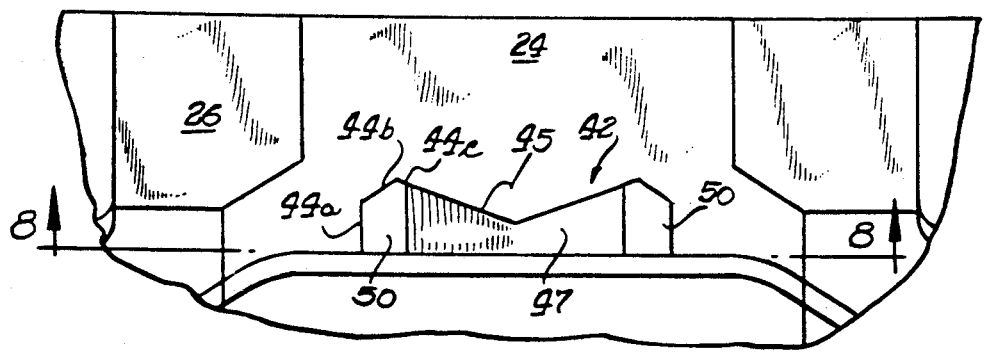
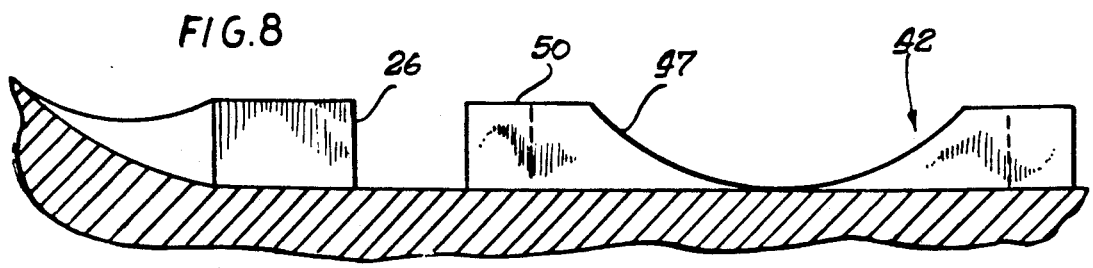

PROSTHETIC HEART VALVE

BACKGROUND OF THE INVENTION

The present invention pertains to heart valve prostheses and in particular, to prosthetic heart valves using pivotable valve members, including bi-leaflet valves.

DESCRIPTION OF THE PRIOR ART

Various types of heart valve prostheses have been developed which operate hemodynamically as a result of the pumping action of the heart. Among the types of heart valves which have been developed are valves having single occluders which pivot along an eccentric axis to open and close the heart valves, such as that described in U.S. Pat. Nos. 4,011,601, 4,423,525 and 4,425,670, and bi-leaflet heart valves, such as those described in U.S. Pat. Nos. 4,484,365 and 4,535,484. The above-mentioned patents illustrate various arrangements for pivotally connecting the valve members or occluders to a valve body and disclose occluders of a variety of shapes. However, most of these designs have never become commercial because of some shortcoming, and the need continues for improved prosthetic heart valves for permanent implantation into the human heart.

In its open position, a prosthetic valve should provide a passageway which is large and which has good flow characteristics so that blood flows freely therethrough without adverse boundary layer separation and with a minimum of drag. The heart valve should be responsive to blood flow to quickly open during the pumping stroke of the heart and to close quickly when the heart relaxes to prevent substantial regurgitation of the blood. The opening and closing of the valve should be sufficiently soft so that the patient is not disturbed by the sounds produced. The heart valve must, of course, be biocompatible and thrombo-resistant, and in this regard, it is important that all surfaces be well washed by blood to prevent stagnation which might lead to eventual clotting. Furthermore, the action of the valve should be such that it does not cause hemolysis (damaging of blood cells), and of course, the heart valve should be constructed to withstand countless openings and closings.

SUMMARY OF THE INVENTION

The present invention provides heart valves having the aforementioned desirable characteristics wherein the valve occluders are designed to promptly open and close in response to reversal of the flow of blood and to eliminate flutter in the open position, thereby resulting in excellent operating characteristics.

These and other objects of the present invention, which will become apparent from studying the appended description and accompanying drawings, are provided in a prosthetic heart valve for allowing blood flow therethrough in a downstream direction. The valve comprises a generally annular valve body having an interior sidewall which defines a central passageway therethrough for the passage of blood in a downstream direction and occluder means mounted in the valve body to alternately permit the flow of blood therethrough in a downstream direction and block blood flow in the reverse direction. The valve body and occluder means have a pivot arrangement by which said occluder means is mounted to pivot between an open position and a closed position where blood flow is blocked, which pivot arrangement includes a pair of projections extending inward from the sidewall and a pair of notches in the occluder means for receiving the projections.

Each of the projections may be formed with upstream and downstream flat surfaces oriented at a predetermined angle to each other, and each of the notches may have complementary surfaces.

In another aspect, each of the projections may be formed with at least one flat surface, with each notch having at least one flat surface and a curved surface extending from the downstream edge of the flat surface. In this instance the flat surfaces are positioned so that, when the occluder means is in the open position, the flat surface on each projection is in surface-to-surface contact with the flat surface in each notch so that, upon reversal of flow of blood through said valve body, the occluder means is immediately displaced slightly upstream causing the curved notch surface to engage the downstream edge of the flat surface of the projection which results in the occluder means immediately beginning to pivot toward its closed position as such upstream displacement begins.

BRIEF DESCRIPTION OF THE DRAWINGS

In the drawings, wherein like elements are referenced alike,

FIG. 4 is a fragmentary view of a leaflet from the valve shown in FIG. 1.

FIG. 5 is a perspective, fragmentary, view of the leaflet shown in FIG. 4, particularly illustrating the notch in the extension of the leaflet;

FIG. 6 is a fragmentary, plan view of the valve body particularly illustrating a flat wall portion of the valve body and a pivot projection extending therefrom;

FIG. 7 is an enlarged fragmentary view of the pivot projection and abutments;

FIG. 8 is an enlarged cross-sectional view of the pivot projection taken along the line 3—3 of FIG. 3;

DETAILED DESCRIPTION OF THE PREFERRED EMBODIMENTS

FIGS. 1-12 show a preferred embodiment of a heart valve prosthesis constructed according to principles of the present invention. The heart valve, generally designated at 10 is of a bi-leaflet construction, but it will be readily apparent to one ordinarily skilled in the art that the principles of the present invention can be applied to a prosthetic heart valve having single occluder or single leaf construction.

Both versions attain numerous advantages as will be described herein; for example, such heart valves will provide an improved flow when the valve is in a fully open position and substantially reduce boundary layer separation at major surfaces of the leaflets, thus minimizing drag, while providing excellent wash characteristics so as to prevent stagnation which might lead to eventual clotting. In addition, such heart valves provide a rapid response upon opening and closing, with a relatively small impact when the leaflets contact the valve body, without hemolysis or like injury to blood cells flowing through the valve.

Figure 1:
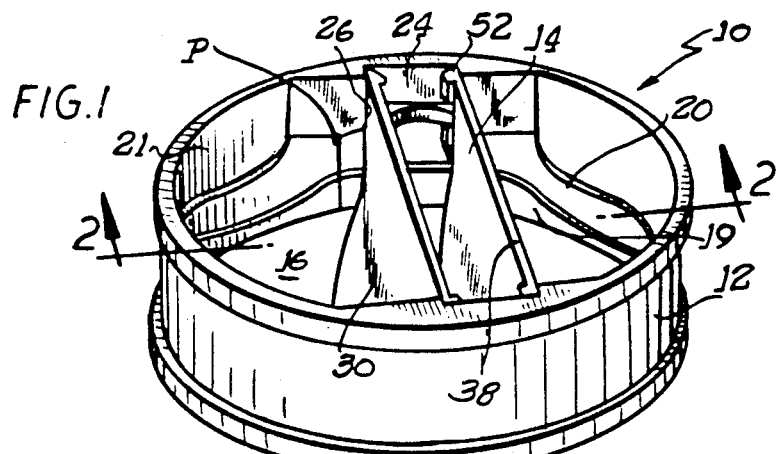
FIG. 1 is a perspective view of a bi-leaflet heart valve embodying various features of the present invention, shown in its open position.
Figure 2:
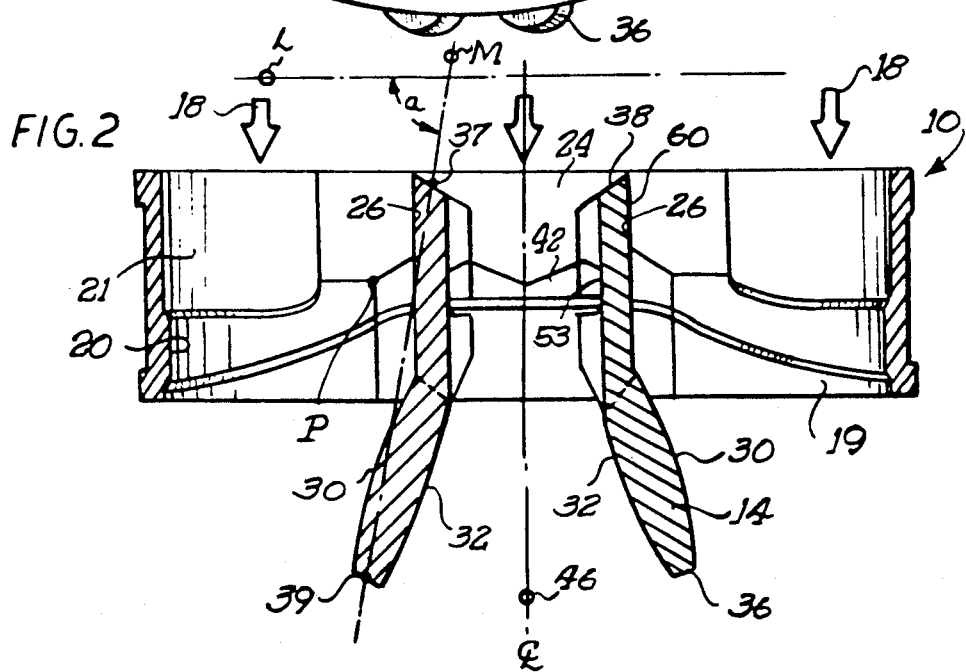
FIG. 2 is an enlarged cross-sectional view of the heart valve taken along the line 2—2 of FIG. 1, showing the valve in its open position.

Referring initially to FIGS. 1-12, heart valve 10 includes a generally annular valve body 12 and carries a pair of pivoting valve occluders or leaflets 14, which open and close to control the normal flow of blood in the downstream direction of arrows 18 (see FIG. 2). Blood flows through passageway 16 which is defined by a generally cylindrical interior surface or sidewall 20 of body 12. Sidewall 20 is interrupted by a pair of diametrically opposed flat wall sections 24. Flanking these flat wall sections are a pair of abutments 26 which act to stop the rotation of the leaflets when the leaflets are in a fully open position, such as that illustrated in FIGS. 1 and 2.

As best seen in FIGS. 6, 7, and 8, pairs of diametrically opposed pivot projections 42 extend generally perpendicularly from the flat wall sections 24. The two lateral sections 43 of the pivot projections 42 each contain three flat seating surfaces 44a, 44b and 44c each oriented between about 110° and about 130°, and preferably approximately 125°, apart from the flat seating surface adjacent to it. In the preferred embodiment, one of the three flat seating surfaces, the first surface 44a, is oriented generally parallel to the axis of blood flow, with the other two surfaces, the second and third surfaces 44b and 44c, lying on the upstream side 45 of the pivot projections 42. (See FIG. 7) The center sections 47 of the pivot projections 42 are concave with respect to the central axis 46 of the valve body 12 so as to minimize the area exposed to, and impeding, the flow of blood through the passageway 16. The front portion 50 of the pivot projections 42 immediately adjacent each lateral section 43 is flat, and generally parallel to the flat wall section 24 of the valve body. Thus, the three seating surfaces 44a, 44b, and 44c of each upstream end of the pivot projections 42 are perpendicular to, and extend between, the parallel surfaces of the flat wall section 24 of the valve body and the flat portion 50 of the pivot projection 42. (See FIGS. 6 and 8) As discussed below, these pivot projections 42 are matingly engaged with notches 53 formed in the leaflets 14.

Referring now to FIG. 2, leaflets 14 have an upstream or inflow surface 30 and an opposed downstream or backflow surface 32. With the cross-sectional view of FIG. 2, which is taken along the central, major axis of the leaflets, it is apparent that the cross-sectional thickness of the leaflets varies considerably from one end of the leaflet to the other. This is to minimize impedance of the heart valve to blood flowing therethrough by employing a three-dimensional composite curvature formed by a cooperation of the leaflet inflow and backflow major surfaces, as described in U.S. patent application Ser. No. 296,428, filed Jan. 28, 1989, the disclosure of which is incorporated herein by reference.

The leaflets 14 have a major arcuate surface 36 which is located at the trailing portions of a fully opened leaflet. A minor surface 38 is located at the opposite, leading end of the leaflet (again, assuming a leaflet in an open position). The curved major surface 36 is preferably arcuate in configuration. The minor surface 38 is preferably of a straight-line configuration so as to present a relatively flat mating surface to the opposing leaflet. This minor surface 38 is tapered inward toward the backflow side 32 of the leaflet 14 at an angle such that the two minor surfaces 38 of the leaflets 14 abut along substantially their entire length when the valve is in the closed position.

Referring to FIGS. 4 and 5, leaflets 14 include a pair of opposed, lateral surfaces 51 which are interposed between the major arcuate mating surface 36 and the minor straight-line mating surface 38. These lateral surfaces 51 of the leaflets are preferably flat, and the leaflets are proportioned so as to provide a minimal clearance 25 with the flat wall sections 24 of the valve body 12 (See FIG. 3). This is to enable the leaflets 14 to pivot adjacent the flat wall sections 24.

Referring to FIG. 5, extending from the backflow surface 32 at the lateral surfaces 51 of both leaflets 14 are extensions 52. These extensions 52 are generally perpendicular to the backflow surface 32, and have an upstream side 54 and downstream side 59. The upstream side 54 of the extension 52 is tapered, or truncated, toward the backflow side 32 of the leaflet 14 so as to form a continuous, smooth surface with the tapered minor surface 38. The opposed major arcuate mating surfaces 36 and the extensions 52 are truncated so as to give the surfaces a substantial thickness which as will now be seen gives several advantages on valve closing. For example, the increased surface area of the mating surfaces 38 distributes forces over a greater area upon contact between mating surfaces, thus reducing stress wear on the leaflets. Also, with the valve in a fully closed position, the increased surface area provides an elongated leakage path between the leaflet mating surface and the valve body. In addition to reducing leakage volume, this latter feature is particularly important in reducing cavitation at the inflow surfaces of the closed leaflets, adjacent the arcuate mating surface.

Figure 12:
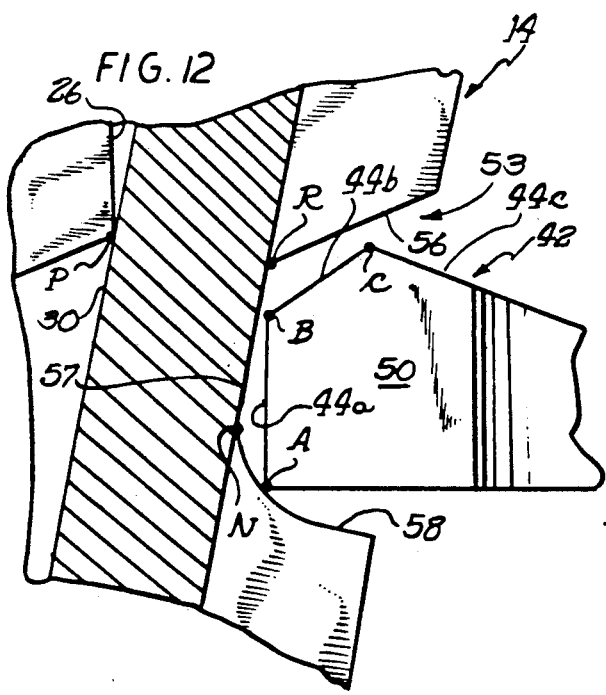
FIG. 12 is an enlarged, fragmentary, cross-sectional view showing the mating engagement between the pivot projection and the leaflet notch as the valve begins its closing movement.
Figure 11:
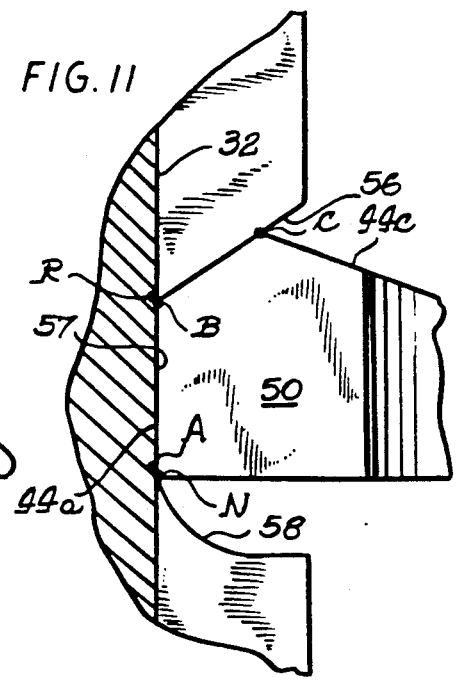
FIG. 11 is an enlarged, fragmentary, cross-sectional view showing the mating engagement between the pivot projection and the leaflet notch with the valve in its open position.

Notches 53 are formed in each extension 52 extending inward from the free end surface 55 of the extension. As best seen in FIGS. 11 and 12, the notches 53 have two flat or straight surfaces 56 and 57 oriented so as to mate with the surfaces 44a and 44b, e.g., at an angle of about 125° with respect to each other, and a third, curved surface 58. In the preferred embodiment, a first straight intermediate surface 57 is substantially parallel and preferably coplanar with the inflow surface 32 of the leaflet, with the second straight leading surface 56 adjacent and on the upstream side thereof (with the leaflet in the open position). Furthermore, the curved surface 58 is adjacent, and on the downstream side of, the first intermediate straight portion 57, and it extends smoothly therefrom, being preferably tangential thereto. The downstream side 59 of the extensions 52 are tapered toward the leaflet 14 to minimize impedance to blood flow through the valve passageway 16.

The leaflets 14 are installed in the valve body 12 by squeezing the body at diametrically opposed locations, i.e. those where the valve body is cut by the reference line 2—2 in FIG. 1. This causes the diametrically opposed flat wall sections 24 to further separate, thus allowing the leaflets 14 to be slid into the passageway 16 of the valve body. The extensions 52 of the leaflets are secured between the ends of the pivot projection 42 and the portion of the valve body which serves as an abutment 26. The flat end portions 50 of the pivot projections 42 are received in the notches 53. The squeezing force is then removed allowing the flat wall sections 24 to return to their original spacing, with a minimal clearance between the flat wall sections 24 of the valve body 12 and the lateral surfaces 51 of the leaflets as discussed above. The notches 53 in the leaflet extensions 52 matingly engage with the pivot projections 42 to allow the leaflets to slidably and pivotally rotate between open and closed positions. This is discussed further below in relation to the operation of the valve.

Figure 3:
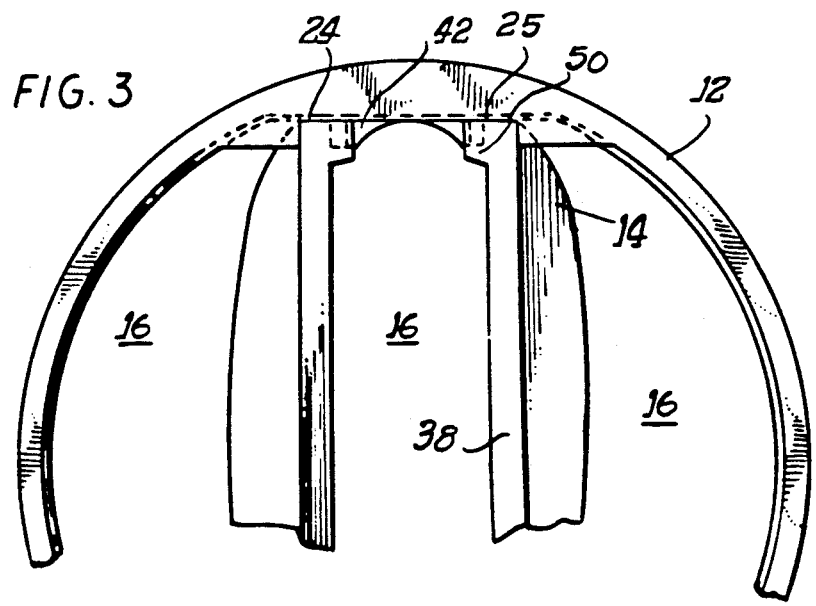
FIG. 3 is a plan view of the bi-leaflet heart valve shown in FIG. 1, showing the valve in an open position.

Referring to FIGS. 3 and 5, the lateral surfaces 51 and extensions 52 of the leaflets 14 are preferably dimensioned to provide a small clearance 25 with the corresponding adjacent flat wall sections 24 of valve body 12.

As will be appreciated by those skilled in the art, the leaflets and heart valve body have relatively simple configurations which are easy to machine and which also provide an improved economical fabrication, in that tolerances of the heart valve components are easily maintained.

The leaflets are slidably and pivotally mounted for rotation between closed and open positions, and it is generally preferred that the opening, and particularly the closing, motions of the leaflets be made as rapid as possible. However, the motion of the end points of the leaflets should be well defined to reduce noise and leaflet wear. For example, the leaflets should not bounce back when contacting seating surfaces defining the end points of their travel, nor should the major surfaces 36 extend beyond the valve body 12 when in a closed position. As will now be seen, such advantages are attained with the present invention.

Figure 9:
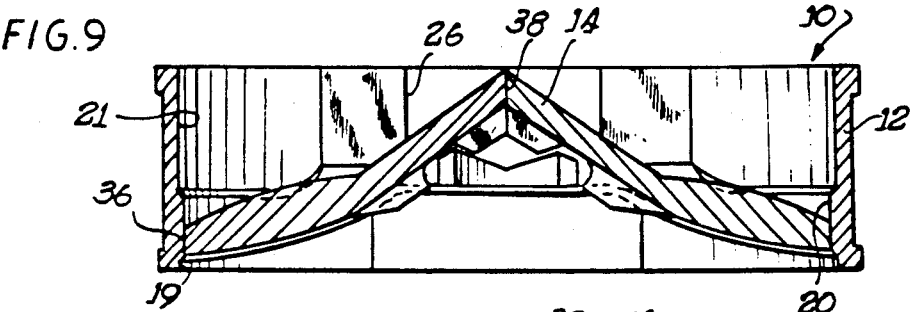
FIG. 9 is a cross-sectional view of the heart valve showing the valve in its closed position.

FIG. 1 shows the inflow surface 30 of leaflets 14 lying adjacent the relatively flat abutments 26 which define the extent of opening of the leaflets, thus fixing one end of their travel. The closing end of the leaflet travel is defined by the contacting of the minor, mating surfaces 38 of the leaflets, and/or the contacting of the major, arcuate, mating surfaces 36 with the interior surface or sidewall 20 of the valve body 12 which has formed therein a seating region at a location between an optional downstream recessed region 19 and an optional upstream recessed region 21, as seen in FIG. 9.

With reference to FIG. 2, abutment 26 in combination with a pivot projection 42, and more particularly the flat seating surfaces 44a and 44b, define the fully open position of leaflets 14. It is generally desirable to orient the fully open leaflets for minimum obstruction of the downstream flow through the valve body passageway 16. As can be seen in FIG. 2, the leading, generally planar portions 60 of the leaflets 14 are oriented generally parallel to the downstream direction of blood flow, generally indicated by arrows 18.

The leaflets 14 undergo a controlled angular displacement between their fully closed and fully open positions. With reference to FIG. 2, the angle of opening (i.e. the angular orientation of the leaflets when in the open position) identified by the reference letter a has a value ranging between about 70° and about 87°. Preferably, the angle of opening of the leaflets has a value ranging between about 70° and about 85°, and most preferably, has an angle ranging between about 77° and about 83°.

As used herein, the term "angle of opening" is defined as the angle between a plane perpendicular to that of the flow through the heart valve (see reference character L in FIG. 2) and the midplane of a fully opened leaflet of that valve. The "midplane of the leaflet" is a flat plane (identified by the reference character M in FIG. 2) which intersects the minor mating surface 38 at a point 37 located halfway between the inflow and backflow leaflet surfaces 30 and 32, and intersects the furthest portion of the major arcuate surface 36 at a point 39 located halfway between the inflow and backflow leaflet surfaces 30 and 32. The plane M bisects minor mating surface 38.

Referring to FIG. 2, the centerline 46 of the passageway 16 through the valve body 10 lies midway between the pivot axes of the pivot projections 42 disposed adjacent a given flat wall section 24. In the fully open position illustrated in FIG. 2, the backflow surfaces of the leaflets 32 lie opposed to one another on opposite sides of the centerline 46, and the portions of the inflow and backflow surfaces 30 and 32 of the leaflets 14 within the valve body 12 extend generally parallel to the central axis 46. In the fully closed position as shown in FIG. 9, the minor, mating surfaces 38 of the leaflets 14 abut one another. No matter which opening angle a is chosen, it is generally preferred that the leaflets 14 are not brought into a straight-line relationship when fully closed, in order to avoid a risk of wedging of the leaflets. Instead, the leaflets 14 should have an angular relation to one another as shown in FIG. 9.

Figure 10:
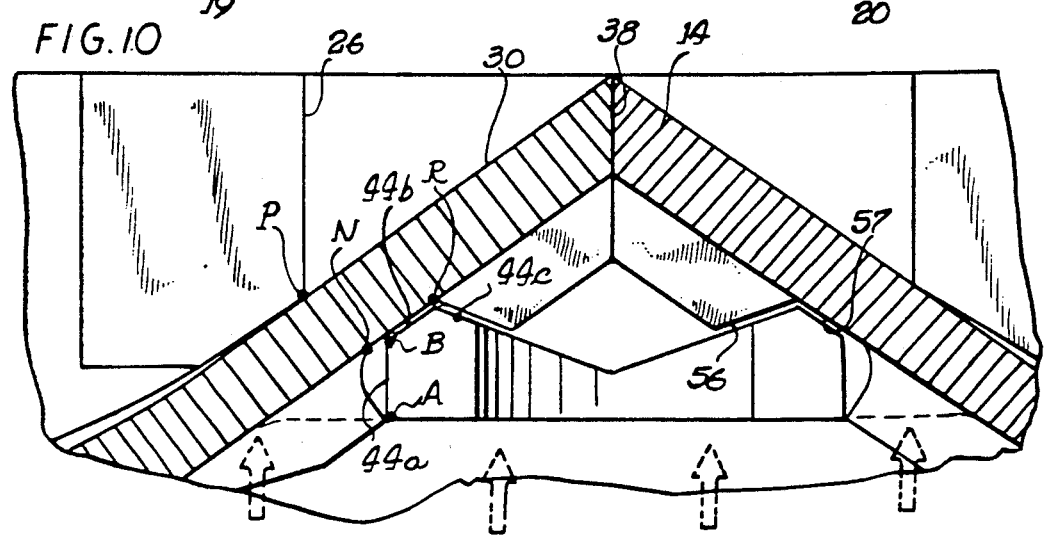
FIG. 10 is an enlarged, fragmentary, cross-sectional view of the mating engagement between the pivot projection and the leaflet notch with the valve in its closed position.

With reference to FIGS. 2 through 14, operation of the heart valve 10 will now be described assuming an initial, fully closed position. In the fully closed position, as shown in FIGS. 9 and 10, the two flat surfaces 56 and 57 of the notch 53 of each of the leaflets lie adjacent to the two upstream flat seating surfaces 44b and 44c of the pivot projection 42, and there is a small clearance between these adjacent surfaces. When the cardiac cycle reverses, blood flows in the direction of the arrows 18 (FIG. 2). During initial valve opening movement, the leaflets are displaced in the downstream direction until the flat surfaces 56 and 57 of the leaflet notches 53 are pressed against the upstream seating surfaces 44b and 44c of the pivot projections 42. Due to the fact that the inflow surfaces 30 of the leaflets have greater surface area on the portions thereof which lie downstream of the pivot projections 42 than on the portions upstream of the pivot projections 42 (FIG. 2), i.e. the notches 53 are located closer to the minor mating surfaces 38 than the major surfaces 36, a moment imbalance is developed between the downstream portions of the inflow surfaces and the upstream portions of the inflow surfaces. This causes the leaflets 14 to begin to pivot about the pivot projections 42 in the direction of valve opening, with their minor mating surfaces 38 being spread apart, and their major surfaces 36 being advanced toward one another. There is no contact of the leaflets with the edge P of abutment 26 during leaflet opening. Pressure on the pivot projections 42 decreases as the leaflets 14 open, due to reduced leaflet cross-sectional area interfering with the blood flow. As the leaflets 14 approach a more open position, the points of contact between the notches 53 and the pivot projections 42 continuously change. The effect of this shifting of the points of contact is discussed below.

Referring now to FIG. 2, the opening movement of the leaflets is stopped when the inflow surfaces 30 thereof contact the flat abutments 26. The abutments 26 are preferably oriented in a direction parallel to the central axis 46 of the valve body so as to orient the fully open leaflets in a direction which presents minimal interference to the blood flow.

In the fully open position, the two flat surfaces 56 and 57 of the leaflet notches 53 are matingly engaged with the first flat seating surface 44a parallel to the flow of blood and the second upstream, flat seating surface 44b immediately adjacent to it (see FIG. 11). The two complementary pairs of surfaces in contact with each other provide a stable, non-fluttering orientation of the leaflet 14 in the fully open position.

Upon a reversal of the cardiac cycle, blood flow develops in an upstream direction, generally opposite that of the arrows 18 of FIG. 2. Referring initially to FIG. 2, the force of back-flowing blood against the leaflet outflow surface 32 causes the leaflets 14 to begin to pivot in a closing direction, and aided by drag forces on the leaflet surfaces, the leaflets are shifted slightly upstream, i.e. in an upward direction as depicted in FIGS. 2, 11, and 12. Upon this shifting of the leaflet, there is engagement between the edge labeled A on the stationary pivot projection 42 and the curved surface 58 of the leaflet notch 53 (see FIG. 12) and contact with the edge P of the downstream surface of the abutment 26. This acts to provide an initial, rapid pivoting of the leaflet 14 in a closing direction which, in turn, exposes a greater portion of the outflow surface 32 of the leaflet to the force of the backflowing bloodstream. As greater portions of the leaflet outflow surfaces 32 become more transversely aligned with the blood stream, the rate of closing may increase.

The closing movement of the leaflets is stopped upon contact between the minor, mating surfaces 38 of the leaflets and/or contact of the major, arcuate surfaces 36 with the interior surface or sidewall 20 of the valve body 12 which has formed therein a seating region at a location between an optional downstream recessed region 19 and an optional upstream recessed region 21, as discussed previously. The seating region merely refers to the remaining area of the right circular cylindrical interior surface of the valve body sidewall 20 lying between the upstream recess 21 and the downstream recess 19, as best seen in FIG. 2. It should be noted that throughout much of the leaflet closing, there is contact between the inflow surface 30 and the edge P on the abutment 26. The leaflets come to rest in the fully closed position of FIGS. 9 and 10, in preparation for reversal of the cardiac cycle and a subsequent opening operation. As can be seen in FIG. 9, in the fully closed position, the major arcuate surface 36 abuts the valve body sidewall 20 in the seating region. As indicated above, the valve body 12 optionally has the recess 21 formed therein, upstream of the sidewall 20, extending along at least a major portion of the length of the sidewall 20.

An advantage of the hinge mechanism of the present invention over conventional hinge mechanisms will now be discussed. The leaflet instantaneous center of rotation (IC), during the closing movement of the leaflet 14 is initially located far from the leaflet surface. This favors a large closing moment which will make the leaflet respond quickly to flow reversal. However, as the closing movement continues, IC migrates resulting in a reduced impact when the leaflet 14 contacts the valve at seating region between recesses 19 and 21, relative to the impact a similar valve member would have rotating on a pivot of circular cross-section. At the beginning of leaflet opening, IC is located where it favors a large opening moment which will make the leaflet respond quickly to flow reversal. As the opening movement continues, IC migrates resulting again in a reduced impact when the leaflet 14 contacts the abutment seat 26.

Thus, valve opening and closing, in a valve constructed according to principles of the present invention, has been found to be free of bounce-back. Also, the seating of the leaflets in a fully closed position has been found to be smooth and reliable, while the seating of the leaflets in the fully open position has been found to be non-fluttering and reliable.

It can be seen from the above that the heart valve 10 constructed according to principles of the present invention has numerous advantages, including economical manufacture of the heart valve components. The cooperation of the inflow and outflow surface configurations of the heart valve leaflet provide unprecedented reductions in drag on blood flow through the fully opened heart valve and complement the aforementioned advantages which result from the pivot design. The surface configurations of the leaflets are not, however, difficult to machine, and preferably consist of combinations of two-dimensionally curvatures.

A description of the present forms of the invention having been described by way of example, it is anticipated that variations of the described forms of the apparatus may be made without departing from the invention and the scope of the appended claims.

What is claimed is:

1. A prosthetic heart valve which comprises
   a generally annular valve body having an interior sidewall which defines a central passageway therethrough for the passage of blood in a downstream direction said annular valve body having an upstream edge and a downstream edge,
   occluder means having an upstream surface and a downstream surface which occluder means is mounted in said valve body to alternately permit the flow of blood therethrough in a downstream direction and block the flow of blood in the reverse direction,
   said valve body and said occluder means having a pivot arrangement by which said occluder means is mounted to pivot between an open position and a closed position where blood flow is blocked;
   said pivot arrangement including a pair of projections extending inward from said sidewall and a pair of notches in said occluder means for receiving said projections;
   each of said projections being formed with first and second flat surfaces oriented at a predetermined angle to each other, said second surface being located upstream of said first surface, and each of said notches having a flat leading surface portion and a flat intermediate surface portion oriented at the same predetermined angle to each other as said projection first and second surfaces, said intermediate surface portion and said first flat surface each having a downstream edge, and
   said flat leading and intermediate surface portions in said notches being positioned so that, when said occluder means is in the open position, said pair of first and second flat surfaces on said projections are respectively in surface-to-surface contact with said flat intermediate and leading surface portions in said notches.

2. A prosthetic heart valve according to claim 1 wherein each of said notches has a curved surface portion extending from the downstream edge of said intermediate surface portion whereby, upon reversal of flow of blood through said valve body, said occluder means is immediately displaced slightly upstream causing said curved notch surface portion to engage the downstream edge of said first flat surface of said projection and resulting in said occluder means immediately beginning to pivot toward its closed position as said upstream displacement begins.

3. A prosthetic heart valve according to claim 1 wherein said valve body includes a pair of abutments extending inward from said interior sidewall, one of said abutments being spaced from each of said projections so that a region of each abutment is engaged by the upstream surface of said occluder means as it pivots from the open to the closed position.

4. A prosthetic heart valve according to claim 3 wherein said first and second flat surfaces of said projections meet along an intermediate straight edge and wherein each said abutment region is located upstream of said intermediate straight edge of said projections.

5. A prosthetic heart valve according to claim 1 wherein said first surface of each said projection is oriented substantially parallel to the centerline of said central passageway.

6. A prosthetic heart valve according to claim 5 wherein said predetermined angle at which said first and second surfaces of said projections are oriented relative to each other is between about 110° and about 130°.

7. A prosthetic heart valve according to claim 1 wherein said occluder means is formed with a generally flat body section, which body section has a pair of depending enlargements extending from the downstream surface thereof, said notches being formed in said enlargements.

8. A prosthetic heart valve according to claim 7 wherein said generally flat occluder body section is aligned substantially parallel to said central passageway centerline in the open position and said occluder means contains a second body section which lies downstream of said generally flat body section and is oriented at an angle of between about 120° and about 160° to the upstream surface of the flat occluder body section.

9. A prosthetic heart valve according to claim 1 wherein said valve body interior sidewall has a pair of diametrically opposed flat wall sections from which said projections and said abutments extend inward.

10. A prosthetic heart valve according to claim 1 wherein said valve body includes four of said projections and said occluder means includes two occluders each having a pair of said notches.

11. A prosthetic heart valve according to claim 10 wherein each of said two occluders has a generally semicircular outer edge and a generally straight inner edge, said inner edges lying adjacent each other in said closed position and said outer edges lying adjacent a seating region of the inner surface of said valve body, said valve body including recess means in said interior sidewall located upstream of said seating region which recess means extends to the upstream edge of said valve body.

12. A prosthetic heart valve which comprises a generally annular valve body having an interior sidewall which defines a central passageway therethrough for the passage of blood in a downstream direction, said valve body having an upstream edge and a downstream edge, occluder means having an upstream surface and a downstream surface, which occluder means is mounted in said valve body to alternately permit the flow of blood therethrough in a downstream direction and block the flow of blood in the reverse direction, said valve body and said occluder means having a pivot arrangement by which said occluder means is mounted to pivot between an open position and a closed position where blood flow is blocked, said pivot arrangement including at least a pair of projections extending inward from said sidewall and at least a pair of notches in said occluder means for receiving said projections, each of said projections being formed with at least one flat surface having a downstream straight edge and each of said notches having at least one flat surface portion having a downstream edge and a curved surface portion extending from said downstream edge of said flat surface portion, and said flat surface portions being positioned in said notches so that, when said occluder means is in the open position, said flat surface on each of said projections is in surface-to-surface contact with said flat surface portion in each of said notches, whereby, upon reversal of flow of blood through said valve body, said occluder means is immediately displaced slightly upstream causing said curved notch surface portion to engage said downstream straight edge of said flat surface of said projection and resulting in said occluder means immediately beginning to pivot toward its closed position as said upstream displacement begins.

13. A prosthetic heart valve according to claim 12 wherein said flat surface of each said projection is oriented substantially parallel to the centerline of said central passageway and said downstream straight edge thereof lies in a plane perpendicular to said centerline.

14. A prosthetic heart valve according to claim 13 wherein said occluder means is formed with a generally flat body section, which body section has a pair of depending enlargements extending from the downstream surface thereof, said notches being formed in said enlargements.

15. A prosthetic heart valve according to claim 14 wherein said generally flat occluder body section is aligned substantially parallel to said central passageway centerline in the open position and said occluder means contains a second body section which lies downstream of said generally flat body section and is oriented at an angle of between about 120° and about 160° to the upstream surface of the flat occluder body section.

16. A prosthetic heart valve according to claim 12 wherein said valve body includes four of said projections and said occluder means includes two occluders each having a pair of said notches.

17. A prosthetic heart valve according to claim 16 wherein each of said two occluders has a generally semicircular outer edge and a generally straight inner edge, said inner edges lying adjacent each other in said closed position and said outer edges lying adjacent a seating region of the inner surface of said valve body, said valve body including recess means in said interior sidewall located upstream of said seating region which recess means extends to the upstream edge of said valve body.

18. A prosthetic heart valve which comprises
a generally annular valve body having an interior sidewall which defines a central passageway therethrough for the passage of blood in a downstream direction,
a pair of occluders which are mounted in said valve body to alternately permit the flow of blood therethrough in a downstream direction and block of the flow of blood in the reverse direction,
said valve body and said occluders having a pivot arrangement by which said occluders are mounted to pivot between an open position and a closed position where blood flow is blocked,
said pivot arrangement including projection means extending inward from diametrically opposite locations on said interior sidewall and a pair of abutments flanking each said projection means and said pivot arrangement also including notch means in each said occluder for receiving said projection means,
said projection means each having a pair of downstream straight edges, each said notch means of said occluder being located so as to receive one of said downstream straight edges of said projection means, and each said notch means also being located to face toward said other occluder when said occluders are in the open position, and each said notch means having a curved surface portion that is located downstream from said downstream edges of said projection means in the open position, and
each said notch means being shaped so that at least portions of said occluders are oriented substantially parallel to the centerline of said central passageway in the open position,
whereby, upon reversal of flow of blood through said valve body, each said occluder is immediately displaced slightly upstream causing said curved notch surface portions to engage said downstream straight edges of said projection means, resulting in said occluders immediately engaging said abutments and beginning to pivot toward the closed position as said upstream displacement begins.

19. A prosthetic heart valve according to claim 18 wherein each said projection means contains a flat surface extending upstream from each said downstream straight edge, which flat surfaces are oriented parallel to the centerline through said central passageway of said valve body, and wherein each said notch means includes a flat surface portion extending upstream from said curved surface portion, which occluder flat surface portion lies in juxtaposed with said projection means flat surface in the open position.

20. A prosthetic heart valve according to claim 19 wherein each said abutment includes a flat surface extending parallel to said valve centerline, a part of each occluder located upstream of said notch means lying in juxtaposed with said flat abutment surface when said occluder is in the open position.

* * * * *

UNITED STATES PATENT AND TRADEMARK OFFICE
CERTIFICATE OF CORRECTION

PATENT NO. :  5,116,366
DATED      :  May 26, 1992
INVENTOR(S) :  Ned H.C. Hwang It is certified that error appears in the above-identified patent and that said Letters Patent is hereby corrected as shown below:

On the title page, Item [75] should read as follows:
Inventors: Ned H.C. Hwang, Memphis, Tenn.
           Jack C. Bokros, Austin, Texas Signed and Sealed this Second Day of November, 1993

*Attest:*

BRUCE LEHMAN

*Attesting Officer*     *Commissioner of Patents and Trademarks*